(12) United States Patent
Phillips et al.

(10) Patent No.: US 7,745,158 B2
(45) Date of Patent: Jun. 29, 2010

(54) **DETECTION OF SECRETED ASPARTYL PROTEASES FROM *CANDIDA* SPECIES**

(75) Inventors: Erica M. Phillips, Woodstock, GA (US); Enrico L. DiGiammarino, Woodstock, GA (US); Kevin P. McGrath, Alpharetta, GA (US)

(73) Assignee: Kimberly-Clark Worldwide, Inc.

( * ) Notice: Subject to any disclaimer, the term of this patent is extended or adjusted under 35 U.S.C. 154(b) by 861 days.

(21) Appl. No.: 11/302,975

(22) Filed: Dec. 14, 2005

(65) Prior Publication Data

US 2007/0134743 A1   Jun. 14, 2007

(51) Int. Cl.
*G01N 33/53* (2006.01)
*G01N 33/558* (2006.01)

(52) U.S. Cl. .................. 435/7.31; 435/7.1; 436/514

(58) Field of Classification Search .................. None
See application file for complete search history.

(56) References Cited

U.S. PATENT DOCUMENTS

| | | | |
|---|---|---|---|
| 3,520,302 A | 7/1970 | Jones |
| 4,168,146 A | 9/1979 | Grubb et al. |
| 4,235,601 A | 11/1980 | Deutsch et al. |
| 4,366,241 A | 12/1982 | Tom et al. |
| 4,442,204 A | 4/1984 | Greenquist et al. |
| 4,603,112 A | 7/1986 | Paoletti et al. |
| 4,614,723 A | 9/1986 | Schmidt et al. |
| 4,722,848 A | 2/1988 | Paoletti et al. |
| 4,769,330 A | 9/1988 | Paoletti et al. |
| 4,801,537 A | 1/1989 | Nagarajan et al. |
| 4,806,472 A | 2/1989 | de Louvencourt et al. |
| 4,966,841 A | 10/1990 | Riley |
| 5,063,158 A | 11/1991 | Schoner et al. |
| 5,075,077 A | 12/1991 | Durley, III et al. |
| 5,174,993 A | 12/1992 | Paoletti |
| 5,208,535 A | 5/1993 | Nakayama et al. |
| 5,252,459 A | 10/1993 | Tarcha et al. |
| 5,266,490 A | 11/1993 | Davis et al. |
| 5,332,660 A | 7/1994 | Takeda et al. |
| 5,338,683 A | 8/1994 | Paoletti |
| 5,395,754 A | 3/1995 | Lambotte et al. |
| 5,405,745 A | 4/1995 | Gorman et al. |
| 5,416,003 A | 5/1995 | Lawrence et al. |
| 5,432,082 A | 7/1995 | Galeotti et al. |
| 5,464,741 A | 11/1995 | Hendrix |
| 5,494,807 A | 2/1996 | Paoletti et al. |
| 5,505,941 A | 4/1996 | Paoletti |
| 5,508,171 A | 4/1996 | Walling et al. |
| 5,518,883 A | 5/1996 | Soini |
| 5,534,132 A | 7/1996 | Vreeke et al. |
| 5,571,684 A | 11/1996 | Lawrence et al. |
| 5,573,909 A | 11/1996 | Singer et al. |
| 5,580,859 A | 12/1996 | Felgner et al. |
| 5,583,023 A | 12/1996 | Cerutti et al. |
| 5,585,273 A | 12/1996 | Lawrence et al. |
| 5,585,279 A | 12/1996 | Davidson |
| 5,589,466 A | 12/1996 | Felgner et al. |
| 5,591,581 A | 1/1997 | Massey et al. |
| 5,591,639 A | 1/1997 | Bebbington |
| 5,604,118 A | 2/1997 | Giri et al. |
| 5,637,509 A | 6/1997 | Hemmilä et al. |
| 5,670,381 A | 9/1997 | Jou et al. |
| 5,674,911 A | 10/1997 | Emanuele et al. |
| 5,731,147 A | 3/1998 | Bard et al. |
| 5,912,228 A | 6/1999 | Lambert, Jr. |
| 5,922,537 A | 7/1999 | Ewart et al. |
| 6,004,530 A | 12/1999 | Sagner et al. |
| 6,004,573 A | 12/1999 | Rathi et al. |
| 6,030,840 A | 2/2000 | Mullinax et al. |
| 6,068,851 A | 5/2000 | Bergeron et al. |
| 6,194,220 B1 | 2/2001 | Malick et al. |
| 6,218,438 B1 | 4/2001 | Alakhov et al. |
| 6,241,863 B1 | 6/2001 | Monbouquette |
| 6,242,268 B1 | 6/2001 | Wieder et al. |

(Continued)

FOREIGN PATENT DOCUMENTS

EP    0343631  A2    11/1989

(Continued)

OTHER PUBLICATIONS

Thorornton et al. Phytopathology, vol. 94, No. 3. pp. 280-288, 2004.*

(Continued)

*Primary Examiner*—Robert Mondesi
*Assistant Examiner*—Khatol Shahnan-Shah
(74) *Attorney, Agent, or Firm*—Dority & Manning, P.A.

(57) ABSTRACT

Methods and devices for the detection of proteins secreted by the hyphal growth form of *Candida* species are disclosed. The disclosed devices may constitute a method for the diagnosis of acute or chronic infections, including candidiasis, caused by microorganisms of the species *Candida*, such as *C. albicans*, for example. The devices of the present invention incorporate antibodies specific to secreted aspartyl protease proteins whose expression is upregulated upon the conversion of the *Candida* species from the commensal to the pathogenic form. The antibodies may be used in assays to allow the diagnosis of candidal infections and disease conditions. Either monoclonal antibodies or polyclonal antibodies may be used, and in the case of the monoclonals, the specific epitopes of the SAP protein may be detected as well as the SAP protein itself.

17 Claims, 6 Drawing Sheets

U.S. PATENT DOCUMENTS

| | | |
|---|---|---|
| 6,251,621 B1 | 6/2001 | Lawrence et al. |
| 6,261,779 B1 | 7/2001 | Barbera-Guillem et al. |
| 6,270,637 B1 | 8/2001 | Crismore et al. |
| 6,281,006 B1 | 8/2001 | Heller et al. |
| 6,316,011 B1 | 11/2001 | Ron et al. |
| 6,362,011 B1 | 3/2002 | Massey et al. |
| 6,444,423 B1 | 9/2002 | Meade et al. |
| 6,461,496 B1 | 10/2002 | Feldman et al. |
| 6,462,030 B1 | 10/2002 | Neurath |
| 6,468,741 B1 | 10/2002 | Massey et al. |
| 6,500,460 B1 | 12/2002 | Bergeron et al. |
| 6,572,875 B2 | 6/2003 | Neurath et al. |
| 6,579,539 B2 | 6/2003 | Lawson et al. |
| 6,582,930 B1 | 6/2003 | Ponomarev et al. |
| 6,585,939 B1 | 7/2003 | Dapprich |
| 6,592,899 B2 | 7/2003 | Fowers et al. |
| 6,596,297 B2 | 7/2003 | Neurath et al. |
| 6,613,583 B1 | 9/2003 | Richter et al. |
| 6,689,569 B2 | 2/2004 | Vojdani |
| 6,706,276 B2 | 3/2004 | Garg et al. |
| 6,822,073 B2 | 11/2004 | Quirk |
| 6,913,759 B2 | 7/2005 | Borgman et al. |
| 2003/0083314 A1 | 5/2003 | Yiv et al. |
| 2003/0118550 A1 | 6/2003 | Kabanov et al. |
| 2003/0119202 A1 | 6/2003 | Kaylor et al. |
| 2003/0124739 A1 | 7/2003 | Song et al. |
| 2003/0133969 A1 | 7/2003 | Bergeron et al. |
| 2003/0139886 A1 | 7/2003 | Bodzin et al. |
| 2003/0166886 A1 | 9/2003 | Leberer et al. |
| 2004/0014061 A1 | 1/2004 | Rupp et al. |
| 2004/0043502 A1 | 3/2004 | Song et al. |
| 2004/0142385 A1 | 7/2004 | Lopez-Ribot |
| 2004/0192642 A1 | 9/2004 | Yang et al. |
| 2004/0241876 A1* | 12/2004 | Fannes ............ 436/514 |
| 2005/0101841 A9 | 5/2005 | Kaylor et al. |
| 2006/0019406 A1 | 1/2006 | Wei et al. |
| 2006/0068500 A1* | 3/2006 | Wei et al. ............ 436/514 |

FOREIGN PATENT DOCUMENTS

| | | |
|---|---|---|
| WO | WO9943343 A1 | 9/1999 |
| WO | WO0003682 A2 | 1/2000 |
| WO | WO 0114533 A2 | 3/2001 |
| WO | WO 0114533 A3 | 3/2001 |
| WO | WO 03089607 A2 | 10/2003 |
| WO | WO 03089607 A3 | 10/2003 |
| WO | WO03105661 A2 | 12/2003 |
| WO | WO 2004036222 A1 | 4/2004 |
| WO | WO2004/093887 A1 | 11/2004 |

OTHER PUBLICATIONS

Abstract of Article—*Adherence of Candida albicans to Components of the Subendothelial Extracellular Matrix*, S. A. Klotz, FEMS Microbiology Letters, vol. 68, No. 3, 1990, pp. 249-253.

Article—*Adsorbed pluronics on the skin of human volunteers: effects on bacterial adhesion*, Marsh et al., International Journal of Pharmaceutics, vol. 251, 2003, pp. 155-163.

Article—*Assessment of PEO/PTMO multiblock copolymer/segmented polyurethane blends as coating materials for urinary catheters: in vitro bacterial adhesion and encrustation behavior*, Park et al., Biomaterials, vol. 23, 2002, pp. 3991-4000.

Article—*Effect of Poloxamer 407 on the Adherence of Pseudomonas aeruginosa to Corneal Epithelial Cells*, Portolés et al., Cornea, vol. 14, No. 1, 1995, pp. 56-61.

Article—*Development and analytic validation of an enzyme-linked immunosorbent assay for the measurement of canine pancreatic lipase immunoreactivity in serum*, Steiner et al., The Canadian Journal of Veterinary Research, vol. 67, 2003, pp. 175-182.

Article—*Differential Candida albicans lipase gene expression during alimentary tract colonization and infection*, Schofield et al., FEMS Microbiology Letters 244, 2005, pp. 359-365.

Article—*Monoclonal antibodies against Candida rugosa lipase*, Rahimi et al., Journal of Molecular Catalysts B: Enzymatic 28, 2004, pp. 71-74.

Search Report and Written Opinion for PCT/US2006/024385, Dec. 12, 2006.

U.S. Appl. No. 11/302,991, filed Dec. 14, 2005, DiGimmarino et al., Detection of Secreted Lipase Protein from *Candida* Species.

U.S. Appl. No. 11/012,758, filed Dec. 15, 2004, Huang et al., Urogenital Infection Inhibition.

Article—*A New Tetradentate β-Diketonate-Europium Chelate That Can Be Covalently Bound to Proteins for Time-Resolved Fluoroimmunoassay*, Yuan et al., Analytical Chemistry, vol. 70, No. 3, Feb. 1, 1998, pp. 596-601.

Article—*An analysis of the Candida albicans genome database for soluble secreted proteins using computer-based prediction algorithms*, Lee et al., Yeast 2003, vol. 20, No. 7, May 2003, pp. 595-610.

Article—*Analysis of secreted aspartic proteinases from Candida albicans: purification and characterization of individual Sap1, Sap2 and Sap3 isoenzymes*, Microbiology, vol. 143, 1997, pp. 349-356.

Article—*Candida albicans Secreted Aspartyl Proteinases in Virulence and Pathogensis*, Naglik et al., Microbiology and Molecular Biology Reviews, vol. 67, No. 3, Sep. 2003, pp. 400-428.

Article—*Cloning and characterization of a gene (LIP1) which encodes a lipase from the pathogenic yeast Candida albicans*, Fu et al., Microbiology, vol. 143, 1997, pp. 331-340.

Article—*Differential Expression of Candida albicans Secreted Aspartyl Proteinase and Phospholipase B Genes in Humans Correlates with Active Oral and Vaginal Infections*, Naglik et al., The Journal of Infectious Diseases, vol. 188, No. 1, Aug. 1, 2003, pp. 469-479.

Article—*Differential secretion of Sap4-6 proteins in Candida albicans during hyphae formation*, Chen et al., Microbiology, vol. 148, 2002, pp. 3743-3754.

Article—*Expression analysis of the Candida albicans lipase gene gamily during experimental infections and in patient samples*, Stehr et al., FEMS Yeast Research 4, 2004, pp. 401-408.

Article—*Identification of Candida by Randomly Amplified Polymorphic DNA Analysis and Differentiation between Candida albicans and Candida dubliniensis by Direct PCR Methods*, Bautista-Muñoz et al., Journal of Clinical Microbiology, vol. 41, No. 1, Jan. 2003, pp. 414-420.

Article—*In Vivo Analysis of Secreted Aspartyl Proteinase Expression in Human Oral Candidiasis*, Naglik et al., Infection and Ummunity, vol. 67, No. 5, May 1999, pp. 2482-2490.

Article—*One-step all-in-one dry reagent immunoassays with fluorescent europium chelate label and time-resolved fluorometry*, Lövgren et al., Clinical Chemistry, vol. 42, No. 8, 1996, pp. 1196-1201.

Article—*Rapid Detection of Candida albicans in Clinical Samples by DNA Amplification of Common Regions from C. albicans-Secreted Aspartic Proteinase Genes*, Flahaut et al., Journal of Clinical Microbiology, vol. 36, No. 2, Feb. 1998, pp. 395-401.

Article—*Secreted lipases of Candida albicans: cloning, characterisation and expression analysis of a new gene family with at least ten members*, Hube et al., Arch. Microbiol., vol. 174, 2000, pp. 362-374.

Thesis of Dan Backman entitled *Interaction Studies of Secreted Aspartic Proteases (Saps) from Candida albicans*, 2005, 53 pages.

Article—*Use of monoclonal antibody in diagnosis of candidiasis caused by Candida albicans: Detection of circulating aspartyl proteinase antigen*, Na Byoung-Kuk et al., Clinical and Diagnostic Laboratory Immunology, vol. 6, No. 6, Nov. 1999, pp. 924-929.

Article—*"Characterization of two monoclonal antibodies against secretory proteinase of Candida tropicalis DSM 4238"*, Borg-Von Zepelin M. et al., Journal of Medical and Veterinary Mycology, vol. 31, No. 1, 1993, pp. 1-15.

\* cited by examiner

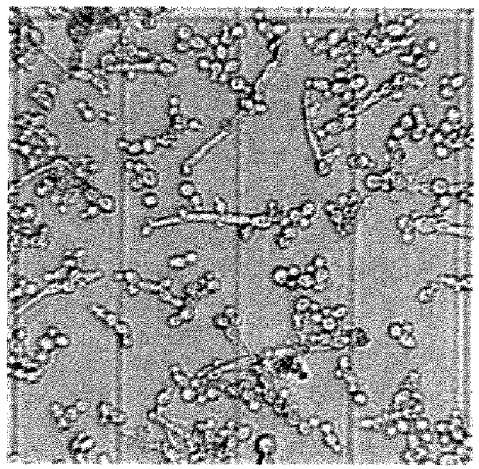 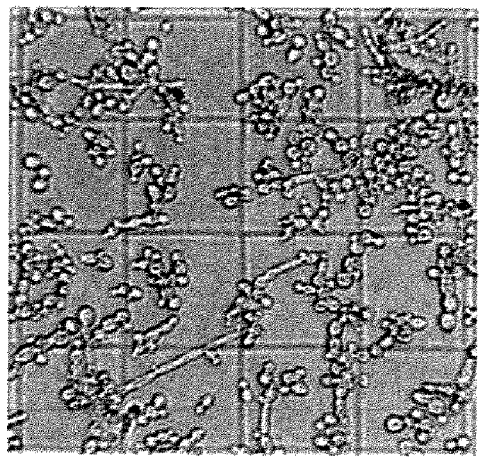
FIG. 7A  FIG. 7B
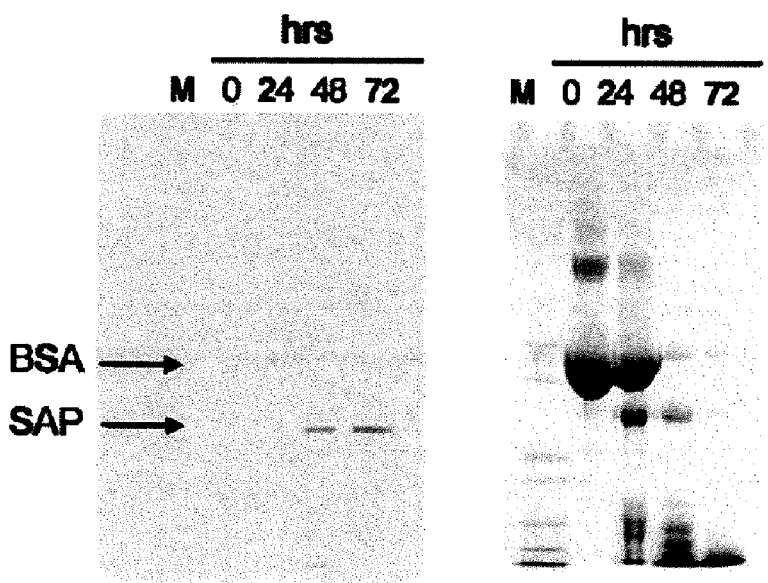
FIG. 8A  FIG. 8B

DETECTION OF SECRETED ASPARTYL PROTEASES FROM *CANDIDA* SPECIES

BACKGROUND OF THE INVENTION

*C. albicans* of the species *Candida* is the most common fungal pathogen of humans and one of the top five most common microorganisms isolated from blood cultures. Normally, *C. albicans* is a benign commensal yeast microbe colonizing mucosal surfaces in the mouth and vagina. Under opportune conditions however, *C. albicans* may become a virulent pathogen able to cause a variety of infections. Depending upon underlying host health and condition, *C. albicans* may cause infections ranging from vulvovaginal candidiasis to life-threatening disseminated candidiasis that is able to infect virtually every organ of the host.

Virulence of *C. albicans* is correlated with a change in morphology of the cell from a spherical form to a filamentous hyphal form. In fact, the morphogenic conversion between yeast and hyphal growth forms appears to be critical in the pathogenesis of invasive candidiasis. Virulence and morphogenic conversion are also associated with a change in the cell's transcriptional profile. For example, among the proteins specifically known to have upregulated expression upon morphogenic conversion are members of the secreted aspartyl protease family.

Among the problems associated with infection caused by *Candida* species such as *C. albicans* is a lack of an accurate diagnostic procedure to recognize the opportunistic form of the cell early on in the disease process. This problem is exacerbated by the fact that there is a broad generality of symptoms for many different infections. For example, among the three most common causes of vaginal infection (vulvovaginal candidiasis, bacterial vaginosis, and trichomoneasis) symptoms may be fairly generic in nature. In addition, concurrent infections may be responsible for symptoms, which may further complicate an accurate diagnosis. In the case of infection due to *C. albicans*, self-treatment is often possible, but this requires an accurate diagnosis.

What is needed in the art are accurate methods and devices for recognizing the opportunistic form of pathogens such as *C. albicans*. For instance, a device that could provide a self-diagnosis route for opportunistic *C. albicans* could be of great benefit to consumers.

SUMMARY OF THE INVENTION

In one embodiment, the present invention is directed to a diagnostic test kit for detecting a secreted aspartyl protease protein within a test sample. The diagnostic test kit may include, for instance, an assay device comprising a fluidic medium. The fluidic medium in turn defines a detection zone within which is immobilized a receptive material. In addition, the detection zone is capable of generating a detection signal that represents the presence or absence of a secreted aspartyl protease protein. The diagnostic kit also includes a detection probe conjugated with a binding member. In accordance with the invention, the receptive material, the binding member, or both contain an antibody that specifically binds to the secreted aspartyl protease protein.

In another embodiment, the invention is directed to a method for detecting the presence of a secreted aspartyl protease protein within a test sample. For example, the method may include contacting an assay device of the invention, for example, an assay device such as that described above, with the test sample and generating a detectable signal at the detection zone that corresponds to the presence or absence of the secreted aspartyl protease protein.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which:

FIGS. 7A and 7B are photographs of *C. albicans* cells following transition to the hyphal form via growth in YBD media;

FIG. 8A illustrates the results of a western blot procedure in which *Candida* culture supernatants were probed against purified SAP3Δ18 polyclonal antibodies generated in the example section;

FIG. 8B illustrates the collodial blue stain of the samples of FIG. 8A;

Figure 1:
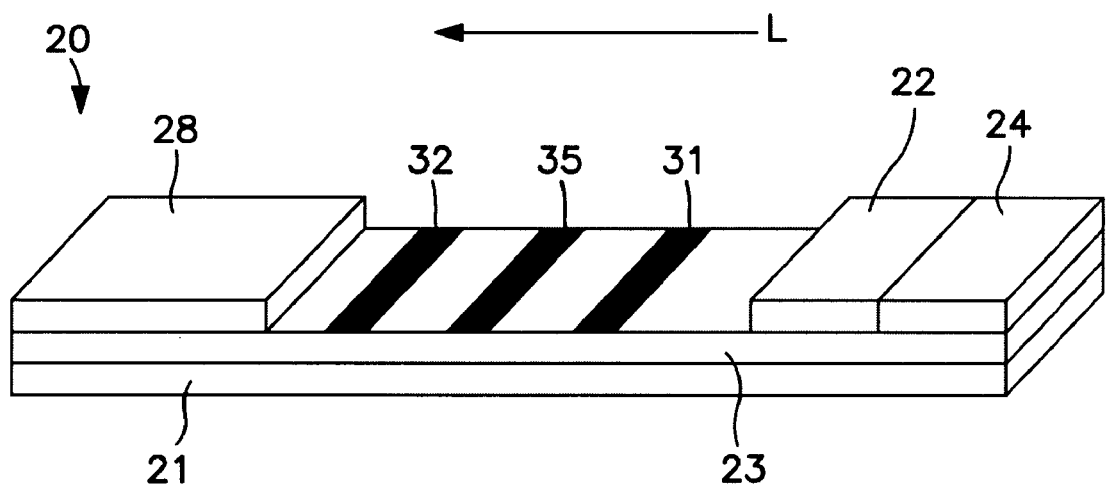
FIG. 1 is a perspective view of one embodiment of a lateral flow assay device of the present invention.

Repeat use of reference characters in the present specification and drawings is intended to represent same or analogous features or elements of the invention.

DETAILED DESCRIPTION OF REPRESENTATIVE EMBODIMENTS

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

DEFINITIONS

"Polypeptide" refers to a molecular chain of amino acids and does not refer to a specific length of the product. Thus, peptides, oligopeptides and proteins are included within the definition of polypeptide. This term is also intended to include polypeptides that have been subjected to post-expression modifications such as, for example, glycosylations, acetylations, phosphorylations, and so forth.

"Protein" refers to any molecular chain of amino acids that is capable of interacting structurally, enzymatically or otherwise with other proteins, polypeptides or any other organic or inorganic molecule.

"Fragment" refers to an amino acid sequence of a protein or polypeptide that is shorter than the entire protein or polypeptide, but contains at least about 25 consecutive amino acids of the full protein or polypeptide.

"Epitope" refers to a part of a protein that specifically binds an antibody by fitting into the antibody-combining site.

"Test sample" refers to a biological material suspected of containing the analyte. The test sample may be derived from any biological source, such as a physiological fluid, including, blood, interstitial fluid, saliva, ocular lens fluid, cerebral spinal fluid, sweat, urine, milk, ascites fluid, mucous, nasal fluid, sputum, synovial fluid, peritoneal fluid, vaginal fluid, menses, amniotic fluid, semen, and so forth. Besides physiological fluids, other liquid samples may be used such as water, food products, and so forth, for the performance of environmental or food production assays. In addition, a solid material suspected of containing the analyte may be used as the test sample. The test sample may be used directly as obtained from the biological source or following a pretreatment to modify the character of the sample. For example, such pretreatment may include preparing plasma from blood, diluting viscous fluids, and so forth. Methods of pretreatment may also involve filtration, precipitation, dilution, distillation, mixing, concentration, inactivation of interfering components, the addition of reagents, lysing, etc. Moreover, it may also be beneficial to modify a solid test sample to form a liquid medium or to release the analyte.

DETAILED DESCRIPTION

In general, the present invention is directed to methods and devices for accurately determining the presence of proteins the expression of which is upregulated by the pathogenic form of *Candida* species. More particularly, the presently disclosed methods and devices may be utilized to accurately detect the presence of members of the secreted aspartyl protease (SAP) family of proteins in a sample via recognition and binding by antibodies specific to the SAP proteins. Accordingly, one embodiment of the present invention is directed to the diagnosis of a yeast infection via recognition of SAP proteins, for instance for diagnosis of vulvovaginal candidiasis caused by opportunistic *C. albicans*.

The invention is not limited to this embodiment, however, and in other embodiments the methods and devices disclosed herein may be beneficially utilized for the detection and diagnosis of other diseases caused by the opportunistic infection of *C. albicans*, such as disseminated candidiasis.

Moreover, *C. albicans* is not the only *Candida* species that is known to possess SAP genes. For example, *C. dubliniensis*, *C. tropicalis*, and *C. parapsilosis* are all known to produce active extracellular proteinases in vitro and are believed to possess SAP genes (see, Naglik, et al., '*Candida albicans* Secreted Aspartyl Proteinases in Virulence and Pathogenesis,' *Microbiology and Molecular Biology Reviews*, Vol. 67, No. 3, p. 400-428 (2003)). As such, in other embodiments, the methods and devices of the present invention may be beneficially utilized in diagnosis of disease caused by other pathogens in which the disease state is characterized by upregulation of SAP protein expression, and in one particular embodiment, for diagnosis of disease caused by other *Candida* pathogens, in addition to the pathogenic *C. albicans* to which the following discussion is primarily directed.

The methods and devices of the present invention utilize antibodies specific to SAP proteins to provide a route for the detection of secreted Candidal antigens present in a biological fluid (e.g. blood, serum, plasma, saliva, urine, cerebrospinal fluid, genitourinary tract) or other biological material (e.g., tissues, bone, muscle, cartilage, or skin). Accordingly, the present invention may constitute a method for the diagnosis of acute or chronic infections, including candidiasis caused by pathogens of the species *Candida*.

The Assay Devices

The devices of the present invention perform heterogeneous immunoassays that incorporate antibodies specific to SAP proteins to allow the detection of the hyphal form of *Candida* species. A heterogeneous assay is an assay in which uncomplexed labeled species are separated from complexed labeled species. Separation may be carried out by physical separation, e.g., by transferring one of the species to another reaction vessel via filtration, centrifugation, chromatography, solid phase capture, magnetic separation, and so forth, and may include one or more washing steps. The separation may also be nonphysical in that no transfer of one or both of the species is conducted, but the species are separated from one another in situ. Heterogeneous immunoassays of the invention utilize the mechanisms of the immune system, i.e., antibodies that are produced in response to the presence of antigens that are pathogenic or foreign to a host organism. These immunoreactants are capable of binding with one another, thereby causing a highly specific reaction mechanism that may be used to determine the presence or concentration of that particular antigen (e.g., SAP protein) in a fluid test sample.

In one preferred embodiment, the assay device of the present invention is a lateral flow assay device. Referring now to FIG. 1, one embodiment of a lateral flow assay device 20 of the present invention will now be described in more detail. As shown, the device 20 contains a porous membrane 23 that acts as a fluidic medium and is optionally supported by a rigid material 21. The fluidic medium of the disclosed lateral flow assay devices is not limited to a porous membrane, however. For instance, in addition to flow through devices that utilize a porous membrane as a fluidic medium, assay devices that utilize one or more fluidic channels or any other suitable component or construct as a fluidic medium are also encompassed by the present invention.

In general, the porous membrane 23 may be made from any of a variety of materials through which the test sample is capable of passing. For example, the materials used to form the porous membrane 23 may include, but are not limited to, natural, synthetic, or naturally occurring materials that are synthetically modified, such as polysaccharides (e.g., cellulose materials such as paper and cellulose derivatives, such as cellulose acetate and nitrocellulose); polyether sulfone; polyethylene; nylon; polyvinylidene fluoride (PVDF); polyester; polypropylene; silica; inorganic materials, such as deactivated alumina, diatomaceous earth, $MgSO_4$, or other inorganic finely divided material uniformly dispersed in a porous polymer matrix, with polymers such as vinyl chloride, vinyl chloride-propylene copolymer, and vinyl chloride-vinyl acetate copolymer; cloth, both naturally occurring (e.g., cotton) and synthetic (e.g., nylon or rayon); porous gels, such as silica gel, agarose, dextran, and gelatin; polymeric films, such as polyacrylamide; and so forth. In one particular embodiment, the porous membrane 23 is formed from nitrocellulose and/or polyether sulfone materials. It should be understood that the term "nitrocellulose" refers to nitric acid esters of cellulose, which may be nitrocellulose alone, or a mixed ester of nitric acid and other acids, such as aliphatic carboxylic acids having from 1 to 7 carbon atoms.

The size and shape of the porous membrane 23 may generally vary as is readily recognized by those skilled in the art. For instance, a porous membrane strip may have a length of from about 10 to about 100 millimeters, in some embodiments from about 20 to about 80 millimeters, and in some embodiments, from about 40 to about 60 millimeters. The width of the membrane strip may range from about 0.5 to about 20 millimeters, in some embodiments from about 1 to about 15 millimeters, and in some embodiments, from about 2 to about 10 millimeters. In one embodiment, the thickness of the membrane strip may be small enough to allow transmission-based detection. For example, the membrane strip may have a thickness less than about 500 micrometers, in some embodiments less than about 250 micrometers, and in some embodiments, less than about 150 micrometers.

As stated above, the support 21 carries the porous membrane 23. For example, the support 21 may be positioned directly adjacent to the porous membrane 23 as shown in FIG. 1, or one or more intervening layers may be positioned between the porous membrane 23 and the support 21. Regardless, the support 21 may generally be formed from any material able to carry the porous membrane 23. The support 21 may be formed from a material that is transmissive to light, such as transparent or optically diffuse (e.g., translucent) materials. Also, it is generally desired that the support 21 is liquid-impermeable so that fluid flowing through the membrane 23 does not leak through the support 21. Examples of suitable materials for the support include, but are not limited to, glass; polymeric materials, such as polystyrene, polypropylene, polyester (e.g., Mylar® film), polybutadiene, polyvinylchloride, polyamide, polycarbonate, epoxides, methacrylates, and polymelamine; and so forth. To provide a sufficient structural backing for the porous membrane 23, the support 21 is generally selected to have a certain minimum thickness. For example, the support 21 may have a thickness that ranges from about 100 to about 5,000 micrometers, in some embodiments from about 150 to about 2,000 micrometers, and in some embodiments, from about 250 to about 1,000 micrometers. For instance, one suitable membrane strip suitable for use as a support having a thickness of about 125 micrometers may be obtained from Millipore Corp. of Bedford, Mass. under the name "SHF180UB25."

As is well known the art, the porous membrane 23 may be cast onto the support 21, wherein the resulting laminate may be die-cut to the desired size and shape. Alternatively, the porous membrane 23 may simply be laminated to the support 21 with, for example, an adhesive. In some embodiments, a nitrocellulose or nylon porous membrane is adhered to a Mylar® film. An adhesive is used to bind the porous membrane to the Mylar® film, such as a pressure-sensitive adhesive. Laminate structures of this type are believed to be commercially available from Millipore Corp. of Bedford, Mass. Still other examples of suitable laminate assay device structures are described in U.S. Pat. No. 5,075,077 to Durley, III, et al., which is incorporated herein in its entirety by reference thereto for all purposes.

The device 20 may also contain an absorbent pad 28. The absorbent pad 28 generally receives fluid that has migrated through the entire porous membrane 23. As is well known in the art, the absorbent pad 28 may assist in promoting capillary action and fluid flow through the membrane 23.

To initiate the detection of an analyte within the test sample, a user may directly apply the test sample to a portion of the porous membrane 23 through which it may then travel in the direction illustrated by arrow "L" in FIG. 1. Alternatively, the test sample may first be applied to a sample pad 24 that is in fluid communication with the porous membrane 23. Some suitable materials that may be used to form the sample pad 24 include, but are not limited to, nitrocellulose, cellulose, porous polyethylene pads, and glass fiber filter paper. If desired, the sample pad 24 may also contain one or more assay pretreatment reagents, either diffusively or non-diffusively attached thereto. For example, in one embodiment, a calibration analyte may be disposed on the sample pad 24 so that it contacts the test sample upon application thereto.

In the illustrated embodiment, the test sample travels from the sample pad 24 to a conjugate pad 22 that is placed in communication with one end of the sample pad 24. The conjugate pad 22 is formed from a material through which the test sample is capable of passing. For example, in one embodiment, the conjugate pad 22 is formed from glass fibers. Although only one conjugate pad 22 is shown, it should be understood that multiple conjugate pads may also be used in the present invention. In one particular embodiment of the present invention, detection and optionally calibration probes (not shown) may be applied to the conjugate pad 22. After application, the probes are then dried to inhibit migration therefrom. The conjugate pad 22 provides a matrix for the deposition of the probes so that they are free to migrate when rehydrated. More specifically, when a liquid test sample contacts the probes, they are rehydrated and become re-suspended and/or re-solubilized. Of course, it should be understood that the probes may be applied to various other locations of the assay device 20 as well, such as directly to the membrane 23, so long as they are capable of being rehydrated by the test sample upon contact therewith.

To facilitate the detection of the SAP protein within a test sample, a detectable substance may be pre-applied to the sample pad and/or conjugate pad, or previously mixed with a diluent or test sample. The detectable substance may function as a detection probe that is detectable either visually or by an instrumental device. Any substance generally capable of producing a signal that is detectable visually or by an instrumental device may be used as detection probes. Suitable detectable substances may include, for instance, luminescent compounds (e.g., fluorescent, phosphorescent, etc.); radioactive compounds; visual compounds (e.g., colored dye or metallic substance, such as gold); liposomes or other vesicles containing signal-producing substances; enzymes and/or substrates, and so forth. Other suitable detectable substances may be described in U.S. Pat. No. 5,670,381 to Jou, et al. and U.S. Pat. No. 5,252,459 to Tarcha, et al., which are incorporated herein in their entirety by reference thereto for all purposes. If the detectable substance is colored, the ideal electromagnetic radiation is light of a complementary wavelength. For instance, blue detection probes strongly absorb red light.

In some embodiments, the detectable substance may be a luminescent compound that produces an optically detectable signal. For example, suitable fluorescent molecules may include, but are not limited to, fluorescein, europium chelates, phycobiliprotein, phycoerythrin, phycocyanin, allophycocyanin, o-phthaldehyde, fluorescamine, rhodamine, and their derivatives and analogs. Other suitable fluorescent compounds are semiconductor nanocrystals commonly referred to as "quantum dots." For example, such nanocrystals may contain a core of the formula CdX, wherein X is Se, Te, S, and so forth. The nanocrystals may also be passivated with an overlying shell of the formula YZ, wherein Y is Cd or Zn, and Z is S or Se. Other examples of suitable semiconductor nanocrystals may also be described in U.S. Pat. No. 6,261,779 to Barbera-Guillem, et al. and U.S. Pat. No. 6,585,939 to Dapprich, which are incorporated herein in their entirety by reference thereto for all purposes.

Further, suitable phosphorescent compounds may include metal complexes of one or more metals, such as ruthenium, osmium, rhenium, iridium, rhodium, platinum, indium, palladium, molybdenum, technetium, copper, iron, chromium, tungsten, zinc, and so forth. Especially preferred are ruthenium, rhenium, osmium, platinum, and palladium. The metal complex may contain one or more ligands that facilitate the solubility of the complex in an aqueous or non-aqueous environment. For example, some suitable examples of ligands include, but are not limited to, pyridine; pyrazine; isonicotinamide; imidazole; bipyridine; terpyridine; phenanthroline; dipyridophenazine; porphyrin; porphine; and derivatives thereof. Such ligands may be, for instance, substituted with alkyl, substituted alkyl, aryl, substituted aryl, aralkyl, substituted aralkyl, carboxylate, carboxaldehyde, carboxamide, cyano, amino, hydroxy, imino, hydroxycarbonyl, aminocarbonyl, amidine, guanidinium, ureide, sulfur-containing groups, phosphorus containing groups, and the carboxylate ester of N-hydroxy-succinimide.

Porphyrins and porphine metal complexes possess pyrrole groups coupled together with methylene bridges to form cyclic structures with metal chelating inner cavities. Many of these molecules exhibit strong phosphorescence properties at room temperature in suitable solvents (e.g., water) and an oxygen-free environment. Some suitable porphyrin complexes that are capable of exhibiting phosphorescent properties include, but are not limited to, platinum (II) coproporphyrin-I and III, palladium (II) coproporphyrin, ruthenium coproporphyrin, zinc(II)-coproporphyrin-I, derivatives thereof, and so forth. Similarly, some suitable porphine complexes that are capable of exhibiting phosphorescent properties include, but not limited to, platinum(II) tetra-meso-fluorophenylporphine and palladium(II) tetra-meso-fluorophenylporphine. Still other suitable porphyrin and/or porphine complexes are described in U.S. Pat. No. 4,614,723 to Schmidt, et al.; U.S. Pat. No. 5,464,741 to Hendrix; U.S. Pat. No. 5,518,883 to Soini; U.S. Pat. No. 5,922,537 to Ewart. et al.; U.S. Pat. No. 6,004,530 to Sagner, et al.; and U.S. Pat. No. 6,582,930 to Ponomarev, et al., which are incorporated herein in their entirety by reference thereto for all purposes.

Bipyridine metal complexes may also be utilized as phosphorescent compounds. Some examples of suitable bipyridine complexes include, but are note limited to, bis[(4,4'-carbomethoxy)-2,2'-bipyridine]2-[3-(4-methyl-2,2'-bipyridine-4-yl)propyl]-1,3-dioxolane ruthenium (II); bis(2,2'bipyridine)[4-(butan-1-al)-4'-methyl-2,2'-bi-pyridine] ruthenium (II); bis(2,2'-bipyridine)[4-(4'-methyl-2,2'-bipyridine-4'-yl)-butyric acid] ruthenium (II); tris(2,2'bipyridine)ruthenium (II); (2,2'-bipyridine) [bis-bis(1,2-diphenylphosphino)ethylene]2-[3-(4-methyl-2,2'-bipyridine-4'-yl)propyl]-1,3-dioxolane osmium (II); bis(2,2'-bipyridine)[4-(4'-methyl-2,2'-bipyridine)-butylamine] ruthenium (II); bis(2,2'-bipyridine)[1-bromo-4(4'-methyl-2,2'-bipyridine-4-yl)butane]ruthenium (II); bis(2,2'-bipyridine)maleimidohexanoic acid, 4-methyl-2,2'-bipyridine-4'-butylamide ruthenium (II), and so forth. Still other suitable metal complexes that may exhibit phosphorescent properties may be described in U.S. Pat. No. 6,613,583 to Richter, et al.; U.S. Pat. No. 6,468,741 to Massey, et al.; U.S. Pat. No. 6,444,423 to Meade, et al.; U.S. Pat. No. 6,362,011 to Massey, et al.; U.S. Pat. No. 5,731,147 to Bard, et al.; and U.S. Pat. No. 5,591,581 to Massey, et al., which are incorporated herein in their entirety by reference thereto for all purposes.

In some cases, luminescent compounds may have a relatively long emission lifetime and/or may have a relatively large "Stokes shift." The term "Stokes shift" is generally defined as the displacement of spectral lines or bands of luminescent radiation to a longer emission wavelength than the excitation lines or bands. A relatively large Stokes shift allows the excitation wavelength of a luminescent compound to remain far apart from its emission wavelengths and is desirable because a large difference between excitation and emission wavelengths makes it easier to eliminate the reflected excitation radiation from the emitted signal. Further, a large Stokes shift also minimizes interference from luminescent molecules in the sample and/or light scattering due to proteins or colloids, which are present with some body fluids (e.g., blood). In addition, a large Stokes shift also minimizes the requirement for expensive, high-precision filters to eliminate background interference. For example, in some embodiments, the luminescent compounds have a Stokes shift of greater than about 50 nanometers, in some embodiments greater than about 100 nanometers, and in some embodiments, from about 100 to about 350 nanometers.

For example, exemplary fluorescent compounds having a large Stokes shift include lanthanide chelates of samarium (Sm (III)), dysprosium (Dy (III)), europium (Eu (III)), and terbium (Tb (I)). Such chelates may exhibit strongly red-shifted, narrow-band, long-lived emission after excitation of the chelate at substantially shorter wavelengths. Typically, the chelate possesses a strong ultraviolet excitation band due to a chromophore located close to the lanthanide in the molecule. Subsequent to excitation by the chromophore, the excitation energy may be transferred from the excited chromophore to the lanthanide. This is followed by a fluorescence emission characteristic of the lanthanide. Europium chelates, for instance, have Stokes shifts of about 250 to about 350 nanometers, as compared to only about 28 nanometers for fluorescein. Also, the fluorescence of europium chelates is long-lived, with lifetimes of about 100 to about 1000 microseconds, as compared to about 1 to about 100 nanoseconds for other fluorescent labels. In addition, these chelates have narrow emission spectra, typically having bandwidths less than about 10 nanometers at about 50% emission. One suitable europium chelate is N-(p-isothiocyanatobenzyl)-diethylene triamine tetraacetic acid-$Eu^{+3}$.

In addition, lanthanide chelates that are inert, stable, and intrinsically fluorescent in aqueous solutions or suspensions may also be used in the present invention to negate the need for micelle-forming reagents, which are often used to protect chelates having limited solubility and quenching problems in aqueous solutions or suspensions. One example of such a chelate is 4-[2-(4-isothiocyanatophenyl)ethynyl]-2,6-bis([N,N-bis(carboxymethyl)amino]methyl)-pyridine [Ref: Lovgren, T., et al.; Clin. Chem. 42, 1196-1201 (1996)]. Several lanthanide chelates also show exceptionally high signal-to-noise ratios. For example, one such chelate is a tetradentate β-diketonate-europium chelate [Ref: Yuan, J. and Matsumoto, K.; Anal. Chem. 70, 596-601 (1998)]. In addition to the fluorescent labels described above, other labels that are suitable for use in the present invention may be described in U.S. Pat. No. 6,030,840 to Mullinax, et al.; U.S. Pat. No. 5,585,279 to Davidson; U.S. Pat. No. 5,573,909 to Singer, et al.; U.S.

Pat. No. 6,242,268 to Wieder, et al.; and U.S. Pat. No. 5,637, 509 to Hemmila, et al., which are incorporated herein in their entirety by reference thereto for all purposes.

Detectable substances, such as described above, may be used alone or in conjunction with a particle (sometimes referred to as "beads" or "microbeads"). For instance, naturally occurring particles, such as nuclei, mycoplasma, plasmids, plastids, mammalian cells (e.g., erythrocyte ghosts), unicellular microorganisms (e.g., bacteria), polysaccharides (e.g., agarose), etc., may be used. Further, synthetic particles may also be utilized. For example, in one embodiment, latex microparticles that are labeled with a fluorescent or colored dye are utilized. Although any synthetic particle may be used in the present invention, the particles are typically formed from polystyrene, butadiene styrenes, styreneacrylic-vinyl terpolymer, polymethylmethacrylate, polyethylmethacrylate, styrene-maleic anhydride copolymer, polyvinyl acetate, polyvinylpyridine, polydivinylbenzene, polybutyleneterephthalate, acrylonitrile, vinylchloride-acrylates, and so forth, or an aldehyde, carboxyl, amino, hydroxyl, or hydrazide derivative thereof. Other suitable particles may be described in U.S. Pat. No. 5,670,381 to Jou, et al.; U.S. Pat. No. 5,252,459 to Tarcha, et al.; and U.S. Patent Publication No. 2003/0139886 to Bodzin, et al., which are incorporated herein in their entirety by reference thereto for all purposes. Commercially available examples of suitable fluorescent particles include fluorescent carboxylated microspheres sold by Molecular Probes, Inc. under the trade names "FluoSphere" (Red 580/605) and "TransfluoSphere" (543/620), as well as "Texas Red" and 5- and 6-carboxytetramethylrhodamine, which are also sold by Molecular Probes, Inc. In addition, commercially available examples of suitable colored, latex microparticles include carboxylated latex beads sold by Bang's Laboratory, Inc. Metallic particles (e.g., gold particles) may also be utilized in the present invention.

When utilized, the shape of the particles may generally vary. In one particular embodiment, for instance, the particles are spherical in shape. However, it should be understood that other shapes are also contemplated by the present invention, such as plates, rods, discs, bars, tubes, irregular shapes, etc. In addition, the size of the particles may also vary. For instance, the average size (e.g., diameter) of the particles may range from about 0.1 nanometers to about 100 microns, in some embodiments, from about 1 nanometer to about 10 microns, and in some embodiments, from about 10 to about 100 nanometers.

In some instances, it may be desired to modify the detection probes so that they are more readily able to bind to the analyte. In such instances, the detection probes may be modified with certain specific binding members that are adhered thereto to form conjugated probes. For instance, the detection probe may be conjugated with antibodies as are further described below that are specific to SAP proteins. The detection probe antibody may be a monoclonal or polyclonal antibody or a mixture(s) or fragment(s) thereof.

The antibodies may generally be attached to the detection probes using any of a variety of well-known techniques. For instance, covalent attachment of the antibodies to the detection probes (e.g., particles) may be accomplished using carboxylic, amino, aldehyde, bromoacetyl, iodoacetyl, thiol, epoxy and other reactive or linking functional groups, as well as residual free radicals and radical cations, through which a protein coupling reaction may be accomplished. A surface functional group may also be incorporated as a functionalized co-monomer as the surface of the detection probe may contain a relatively high surface concentration of polar groups. In addition, although detection probes are often functionalized after synthesis, such as with poly(thiophenol), the detection probes may be capable of direct covalent linking with an antibody without the need for further modification. For example, in one embodiment, the first step of conjugation is activation of carboxylic groups on the probe surface using carbodiimide. In the second step, the activated carboxylic acid groups are reacted with an amino group of an antibody to form an amide bond. The activation and/or antibody coupling may occur in a buffer, such as phosphate-buffered saline (PBS) (e.g., pH of 7.2) or 2-(N-morpholino) ethane sulfonic acid (MES) (e.g., pH of 5.3). The resulting detection probes may then be contacted with ethanolamine, for instance, to block any remaining activated sites. Overall, this process forms a conjugated detection probe, where the antibody is covalently attached to the probe. Besides covalent bonding, other attachment techniques, such as physical adsorption, may also be utilized in the present invention.

In one embodiment, the antibody may be detectably labeled by linking to an enzyme. The enzyme, in turn, when later exposed to a substrate, will react with the substrate in such a manner as to produce a chemical moiety which may be detected as, for example, by spectrophotometric or fluorometric means. Examples of enzymes which may be used to detectably label the antibodies as herein described include malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholine esterase.

Another technique that may also result in greater sensitivity when used in conjunction with the present invention consists of coupling the antibodies to low molecular weight haptens. The haptens may then be specifically detected by means of a second reaction. For example, it is common to use such haptens as biotin (reacting with avidin) or dinitrophenol, pyridoxal and fluorescamine (reacting with specific antihapten antibodies) in this manner.

The antibodies of the present invention also may be detectably labeled by coupling to a chemiluminescent compound. The presence of the chemiluminescent-tagged antibody is then determined by detecting the presence of luminescence that arises during the course of the chemical reaction. Examples of particularly useful chemiluminescent labeling compounds are luminol, isoluminol, theromatic acridinium ester, imidazole, acridinium salt and oxalate ester. Likewise, a bioluminescent compound may be used to label the antibodies as further described below. Bioluminescence is a type of chemiluminescence found in biological systems in which a catalytic protein increases the efficiency of the chemiluminescent reaction. The presence of a bioluminescent reagent is determined by detecting the presence of luminescence. Important bioluminescent compounds for purposes of labeling are luciferin, luciferase and aequorin.

Referring again to FIG. 1, the porous membrane 23 also defines various zones configured to perform the assay. For instance, the porous membrane 23 defines a detection zone 31 that contains a receptive material that is capable of binding to the conjugated detection probes (or complexes thereof) that pass through the length of the membrane 23. The receptive material is immobilized on the porous membrane 23 and may be an antibody that is the same or different from the antibody of the conjugated detection probe. In one embodiment, the two antibodies may be different. For example, the receptive material may include a first monoclonal antibody specific to a first epitope of an SAP protein, and the antibody of the conjugated detection probe may be a second, different monoclonal antibody specific to a second epitope of the SAP protein. In sandwich assay formats, for example, the receptive material may serve as a stationary binding site for complexes formed between the SAP proteins in the test sample and the conjugated detection probes. Specifically, the SAP proteins have two or more binding sites (e.g., epitopes). Upon reaching the detection zone 31, one of these binding sites is occupied by the antibody of the conjugated probe. However, a free binding site of the SAP protein may bind to the immobilized first receptive material. Upon being bound to the immobilized receptive material, the complexed probes form a new ternary sandwich complex.

Other than the detection zone 31, the lateral flow device 20 may also define various other zones for enhancing detection accuracy. For example, in embodiments in which high analyte concentrations are a concern, the assay device 20 may contain an indicator zone 35 that is positioned downstream from the detection zone 31 and is configured to provide information as to whether the analyte concentration has reached the saturation concentration ("hook effect" region) for the assay. The indicator zone 35 contains a second receptive material that is immobilized on the membrane 23 and serves as a stationary binding site for the conjugated detection probes. To accomplish the desired binding within the indicator zone 35, it is generally desired that the second receptive material is capable of differentiating between those detection probes that are complexed with the SAP proteins and those that remain uncomplexed. For example, in one embodiment, the second receptive material includes a molecule that has at least one epitope in common with the SAP proteins, such as entire protein molecules, or derivatives or fragments (e.g., analogs) thereof, so that it is capable of specifically binding to an antibody conjugate when it is uncomplexed with the SAP proteins in the sample.

Although the detection zone 31 and optional indicator zone 35 may provide accurate results, it is sometimes difficult to determine the relative concentration of the analyte within the test sample under actual test conditions. Thus, the assay device 20 may include a calibration zone 32. In this embodiment, the calibration zone 32 is formed on the membrane 23 and is positioned downstream from the detection zone 31 and optional indicator zone 35. Alternatively, however, the calibration zone 32 may also be positioned upstream from the detection zone 31 and/or optional indicator zone 35. The calibration zone 32 is provided with a third receptive material that is capable of binding to any calibration probes that pass through the length of the membrane 23. When utilized, the calibration probes may contain a detectable substance that is the same or different than the detectable substance used for the detection probes. Moreover, the calibration probes may also be conjugated with a specific binding member for the SAP proteins. For example, in one embodiment, biotinylated calibration probes may be used. Generally speaking, the calibration probes are selected in such a manner that they do not bind to the first or second receptive material at the detection zone 31 and indicator zone 35. The third receptive material of the calibration zone 32 may be the same or different than the receptive materials used in the detection zone 31 or indicator zone 35. For example, in one embodiment, the third receptive material is a third antibody specific to the SAP proteins. It may also be desired to utilize various non-biological materials for the third receptive material (e.g., polyelectrolytes) of the calibration zone 32, such as described in U.S. Patent Application Publication No. 2003/0124739 to Song, et al., which is incorporated herein in its entirety by reference thereto for all purposes.

The detection zone 31, indicator zone 35, and calibration zone 32 may each provide any number of distinct detection regions so that a user may better determine the concentration of one or more SAP proteins within a test sample. Each region may contain the same receptive materials, or may contain different receptive materials. For example, the zones may include two or more distinct regions (e.g., lines, dots, etc.). The regions may be disposed in the form of lines in a direction that is substantially perpendicular to the flow of the test sample through the assay device 20. Likewise, in some embodiments, the regions may be disposed in the form of lines in a direction that is substantially parallel to the flow of the test sample through the assay device 20.

In some cases, the membrane 23 may also define a control zone (not shown) that gives a signal to the user that the assay is performing properly. For instance, the control zone (not shown) may contain an immobilized receptive material that is generally capable of forming a chemical and/or physical bond directly with the detection probes or with the receptive material antibody immobilized on the probes. In addition, it may also be desired to utilize various non-biological materials for the control zone receptive material. For instance, in some embodiments, the control zone receptive material may also include a polyelectrolyte, such as described above, that may bind to uncaptured probes. Because the receptive material at the control zone is only specific for probes, a signal forms regardless of whether the analyte is present. The control zone may be positioned at any location along the membrane 23, but is preferably positioned downstream from the detection zone 31 and the indicator zone 35.

Qualitative, semi-quantitative, and quantitative results may be obtained in accordance with the present invention. For example, when it is desired to semi-quantitatively or quantitatively detect an analyte, the intensity of any signals produced at the detection zone 31, indicator zone 35, and/or calibration zone 32 may be measured with an optical reader. The actual configuration and structure of the optical reader may generally vary as is readily understood by those skilled in the art. For example, optical detection techniques that may be utilized include, but are not limited to, luminescence (e.g., fluorescence, phosphorescence, etc.), absorbance (e.g., fluorescent or non-fluorescent), diffraction, etc. One suitable reflectance spectrophotometer is described, for instance, in U.S. Patent App. Pub. No. 2003/0119202 to Kaylor, et al., which is incorporated herein in its entirety by reference thereto for all purposes. In another embodiment, a reflectance-mode spectrofluorometer may be used to detect the intensity of a fluorescence signal. Suitable spectrofluorometers and related detection techniques are described, for instance, in U.S. Patent App. Pub. No. 2004/0043502 to Song, et al., which is incorporated herein in its entirety by reference thereto for all purposes. Likewise, a transmission-mode detection system may also be used to signal intensity.

Detection and calibration may be performed automatically and/or manually in accordance with the present invention. For example, a microprocessor may optionally be employed to convert signal intensities from a detector to a result that quantitatively or semi-quantitatively indicates the concentration of the SAP protein in the sample. The microprocessor may include memory capability to allow the user to recall the last several results. Those skilled in the art will appreciate that any suitable computer-readable memory devices, such as RAM, ROM, EPROM, EEPROM, flash memory cards, digital video disks, Bernoulli cartridges, and so forth, may be used. If desired, the results may be conveyed to a user using a liquid crystal (LCD) or LED display.

Although various embodiments of device configurations have been described above, it should be understood, that a device of the present invention may generally have any configuration desired, and need not contain all of the components described above. Various other device configurations, for instance, are described in U.S. Pat. No. 5,395,754 to Lambotte, et al.; U.S. Pat. No. 5,670,381 to Jou, et al.; and U.S. Pat. No. 6,194,220 to Malick, et al., which are incorporated herein in their entirety by reference thereto for all purposes.

Various formats may be used to test for the presence or absence of an SAP protein using the assay devices of the present invention. For instance, a "sandwich" format typically involves mixing the test sample with detection probes conjugated with a specific binding member (e.g., antibody) for the analyte to form complexes between the analyte and the conjugated probes. These complexes are then allowed to contact a receptive material (e.g., antibodies) immobilized within the detection zone. Binding occurs between the analyte/probe conjugate complexes and the immobilized receptive material, thereby localizing "sandwich" complexes that are detectable to indicate the presence of the analyte. This technique may be used to obtain quantitative or semi-quantitative results. Some examples of such sandwich-type assays are described by U.S. Pat. No. 4,168,146 to Grubb, et al. and U.S. Pat. No. 4,366,241 to Tom, et al., which are incorporated herein in their entirety by reference thereto for all purposes. In a competitive assay, the labeled probe is generally conjugated with a molecule that is identical to, or an analog of, the analyte. Thus, the labeled probe competes with the analyte of interest for the available receptive material. Competitive assays are typically used for detection of analytes such as haptens, each hapten being monovalent and capable of binding only one antibody molecule. Examples of competitive immunoassay devices are described in U.S. Pat. No. 4,235,601 to Deutsch, et al., U.S. Pat. No. 4,442,204 to Liotta, and U.S. Pat. No. 5,208,535 to Buechler, et al., which are incorporated herein in their entirety by reference thereto for all purposes. Various other device configurations and/or assay formats are also described in U.S. Pat. No. 5,395,754 to Lambotte, et al.; U.S. Pat. No. 5,670,381 to Jou, et al.; and U.S. Pat. No. 6,194,220 to Malick, et al., which are incorporated herein in their entirety by reference thereto for all purposes.

Although various assay device configuration have been described herein, it should be understood that any known assay device may be utilized that is capable of incorporating an antibody in accordance with the present invention. For example, electrochemical affinity assay devices may also be utilized, which detect an electrochemical reaction between an SAP protein (or complex thereof) and a capture ligand on an electrode strip. For example, various electrochemical assays and assay devices are described in U.S. Pat. No. 5,508,171 to Walling, et al.; U.S. Pat. No. 5,534,132 to Vreeke, et al.; U.S. Pat. No. 6,241,863 to Monbouquette; U.S. Pat. No. 6,270,637 to Crismore, et al.; U.S. Pat. No. 6,281,006 to Heller, et al.; and U.S. Pat. No. 6,461,496 to Feldman, et al., which are incorporated herein in their entirety by reference thereto for all purposes.

Diagnostic Kits

The present invention is also directed to kits for performing the disclosed assays. The kits may include antibodies to SAP proteins and/or fragments thereof as described herein (raised against whole SAP proteins or active immunoreactive fragments or analogs thereof) which may be optionally immobilized, as well as any necessary reagents and equipment to prepare the biological sample for and to conduct analysis, e.g. preservatives, reaction media such as nontoxic buffers, microtiter plates, micropipettes, etc. The antibodies may be lyophilized or cryopreserved. The types of immunoassays that may be incorporated in kit form are many. In one embodiment, the antibodies of the invention as set forth above may be used in kits to provide a method for self-diagnosis of a candidal infection. Such diagnostic kits may be prepared so as to be suitable for determining the presence of SAP proteins that will bind to the antibodies of the invention. These diagnostic kits will generally include the antibodies as herein described along with suitable means for detecting binding by that antibody such as would be readily understood by one skilled in this art. For example, the means for detecting binding of the antibody may comprise a detectable label that is linked to the antibody as described above. These kits may then be used in diagnostic methods to detect the presence of a candidal infection in a sample through determination of whether the antibodies bind to analytes in the sample, which would indicated the presence of such microorganisms either in the sample itself or in the source.

In one particular embodiment, a kit of the present invention may be useful in methods of monitoring the level of Candidal antibodies or antigens in a test sample obtained from a human or animal. For example, the kit may be useful in monitoring the level of Candidal antibodies or antigens in vaginal fluid, whole blood or serum, saliva, urine, or the like. If monitoring the level of Candidal antigen is desired, the kit may include a Candidal antibody in accordance with the present invention as described herein along with a means of determining the level of binding to that antibody. When it is desired to measure the level of Candidal antibodies in a sample, the kit will preferably include an isolated Candidal epitopic carbohydrate moietyprotein, or peptide such as described herein, e.g., a protein or peptide selected from the group consisting of the SAP proteins along with means for detecting binding of those antigens to Candidal antibodies present in the sample.

The Antibodies

The antibodies of the disclosed devices may be monoclonal or polyclonal and may be generated using any suitable method as is known to one of skill in the art. For example, in one embodiment, one or more isolated and/or purified or recombinantly produced SAP proteins may be utilized to generate the antibodies.

A family of 10 SAP genes encodes the SAP proteins expressed by *C. albicans*. Eight of the *C. albicans* proteins (SAP1-SAP8) are known to be secreted, while SAP9 and SAP10 have putative GPI-anchors and thus may not be secreted. A large volume of information concerning these proteins as well as their encoding genes is generally known to one of ordinary skill in the art and available from many sources such as, for example, the *Candida* genome database (www.candidagenome.org). Names and identifiers of these 10 SAP genes are summarized below in Table 1.

TABLE 1

| STANDARD NAME | SYSTEMATIC NAME | ALIAS | GENBANK ACCESSION NUMBER |
|---|---|---|---|
| SAP1 | orf19.5714 | orf19.13137, PRA10, CAP, PEP1, IPF21467.1, IPF8101.2, Contig4-2608_0006, orf6.4644, PEP10, OP1A | L12451 |
| SAP2 | orf19.3708 | orf19.11193, PRA11, SAP2x, IPF23558.1, IPF9220.2, Contig4-2800_0001, orf6.5306, PRA, CAP, PEP, PEP11 | M83663, AF481101 |
| SAP3 | orf19.6001 | orf19.13422, IPF21229.1, IPF8313.1, Contig4-1997_0001, orf6.9036 | L22358 |
| SAP4 | orf19.5716 | orf19.13139, IPF21464.1, IPF8099.1, Contig4-2038_0003, orf6.3803 | L25388 |
| SAP5 | orf19.5585 | orf19.13032, IPF21596.1, IPF6816.1, Contig4-2830_0009, orf6.4427 | Z30191 |
| SAP6 | orf19.5542 | orf19.12988, IPF12747.2, IPF9135.2, Contig4-2734_0005, orf6.2204, orf6.3624 | Z30192 |
| SAP7 | orf19.756 | orf19.8376, IPF19935.1, IPF29700.1, Contig4-2608_0006, orf6.3635 | Z30193 |
| SAP8 | orf19.242 | orf19.7872, IPF27022.1, IPF10508.1, Contig4-2868_0016, orf6.2688 | AF043330 |
| SAP9 | orf19.6928 | orf19.14190, IPF20187.1, IPF4215.2, Contig4-2390_0003, orf6.7314 | AF043331 |
| SAP10 | orf19.3839 | orf19.11320, orf6.7534, IPF23460.1, IPF4089.1, Contig4-3060_0016 | AF146440 |

In one embodiment, nucleic acids encoding one or more of the SAP proteins or immunogenic epitopes thereof may be expressed and purified to obtain suitable quantity of protein that may then be utilized to generate the antibodies of the disclosed invention. For instance, recombinant expression of a SAP protein or targeted segment thereof may include amplifying a targeted nucleotide sequence encoding the polypeptide from genomic DNA obtained from a *C. albicans* culture and then introducing the nucleotide sequence into an expression vector adapted for use in the desired expression system. The nucleotide sequence of such a construct is not limited to cDNA sequences, however, and the SAP protein-encoding construct may include variations as are known to those of skill in the art including orthologs, homologs, and alleles of the cDNA encoding the SAP proteins, provided the transcribed protein product may exhibit the same or superior immunogenic response in a host as the cDNA encoded transcription products.

The nucleic acid sequence may be introduced and expressed in any host organism, for example, in either prokaryotic or eukaryotic host cells. Examples of host cells include, without limitation, bacterial cells, yeast cells, cultured insect cell lines, and cultured mammalian cells lines. Preferably, the recombinant host cell system that is selected processes and post-translationally modifies nascent peptides in a manner desired to produce the immunogenic polypeptide or protein. In one embodiment, prokaryotic organisms may be utilized, for example, *E. coli*. In other embodiments, however, a eukaryotic host may be preferred, for instance the eukaryotic yeast *P. pastoris*.

The targeted SAP nucleic acid may be placed in expression cassettes for expression in the selected host. Such expression cassettes will comprise a transcriptional initiation region linked to the genetic sequence. Expression cassettes also may have a plurality of restriction sites for insertion of the nucleic acid to be under the transcriptional regulation of various control elements. The expression cassette additionally may contain selectable marker genes. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors may contain endogenous enhancers/promoters, splice junctions, intervening sequences, polyadenylation signals, etc., or a combination of both endogenous and exogenous control elements.

Preferably the nucleic acid in the vector is under the control of, and operably linked to, an appropriate promoter or other regulatory elements for transcription in a host cell. Generally, any suitable promoter may be used that is capable of operative linkage to the heterologous DNA such that transcription of the DNA may be initiated from the promoter by an RNA polymerase that may specifically recognize, bind to, and transcribe the DNA in reading frame. Moreover, while promoters of the present invention may include sequences to which an RNA polymerase binds, this is not a requirement of the invention. For example, promoters of the disclosed DNA constructs may include regions to which other regulatory proteins may bind in addition to regions involved in the control of the protein translation, including coding sequences.

The vector may, if desired, be a bi-functional expression vector that may function in multiple hosts. The transcriptional cassette generally includes in the 5'-3' direction of transcription, a promoter, a transcriptional and translational initiation region, a DNA sequence of the targeted SAP, and a transcriptional and translational termination region functional in the organism. The termination region may be native with the transcriptional initiation region, may be native with the DNA sequence of the targeted SAP, or may be derived from another source.

Nucleic acids encoding entire SAP proteins or immunogenic segments thereof may be introduced into host cells by any method known to one of skill in the art. For example, such nucleic acids may be introduced into bacterial cells by commonly used transformation procedures such as by treatment with calcium chloride or by electroporation. If the polypeptides are to be expressed in eukaryotic host cells, nucleic acids encoding those peptides may be introduced into eukaryotic host cells by a number of means including calcium phosphate co-precipitation, spheroplast fusion, electroporation and so forth. When the eukaryotic host cell is a yeast cell, transformation may be affected by treatment of the host cells with lithium acetate or by electroporation.

A wide range of expression vectors is available in the art. Description of various expression vectors and how to use them may be found in, for example U.S. Pat. Nos. 5,604,118; 5,583,023; 5,432,082; 5,266,490; 5,063,158; 4,966,841; 4,806,472; and 4,801,537; and in Goedel et al., Gene Expression Technology, Methods of Enzymology, Vol. 185, Academic Press, San Diego (1989). Recombinant DNA and molecular cloning techniques that may be used to help make and use aspects of the invention are described by Sambrook et al., Molecular Cloning: A Laboratory Manual Vol. 1-3, Cold Spring Harbor laboratory, Cold Spring Harbor, N.Y. (2001); Ausubel (ed.), Current Protocols in Molecular Biology, John Wiley and Sons, Inc. (1994); T. Maniatis, E. F. Fritsch and J. Sambrook, Molecular Cloning: A Laboratory Manual, Cold Spring Harbor laboratory, Cold Spring Harbor, N.Y. (1989); and by T. J. Silhavy, M. L. Berman, and L. W. Enquist, Experiments with Gene Fusions, Cold Spring Harbor Laboratory, Cold Spring Harbor, N.Y. (1984).

In one embodiment a prokaryotic *E. coli* expression system may be used. Useful *E. coli* vectors may contain constitutive or inducible promoters to direct expression of either fusion or non-fusion proteins. With fusion vectors, a number of amino acids are usually added to the expressed target gene sequence at the amino terminus. Additionally, a proteolytic cleavage site may be introduced at a site between the target recombinant protein and the fusion sequence. Once the fusion protein has been purified, the cleavage site allows the target recombinant protein to be separated from the fusion sequence. Enzymes suitable for use in cleaving the proteolytic cleavage site include Factor Xa and thrombin. Fusion expression vectors which may be useful in the present invention include pGex (Amrad Corp., Melbourne, Australia), pRIT5 (Pharmacia, Piscataway, N.J.) and PMAL (New England Biolabs, Beverly, Mass.), which fuse glutathione S-transferase, protein A, or maltose E binding protein, respectively, to the target recombinant protein.

Expression of unfused foreign genes in *E. coli* may be accomplished with recombinant vectors including, but not limited to, the *E. coli* expression vector pUR278 (Ruther et al., EMBO J. 2:1791, 1983). Using the pUR278 vector, the nucleotide sequence coding for the target gene product may be ligated in frame with the lac V coding region to produce a fusion protein. Other useful vectors include pin vectors (Inouye and Inouye, Nucleic Acids Res. 13:3101-3109, 1985) and so forth.

Expression of the targeted SAP gene may also be obtained using eukaryotic vectors such as mammalian, yeast or insect cells. The use of eukaryotic vectors permits partial or complete glycosylation and/or the formation of the relevant inter- or intra-chain disulfide bonds. Examples of vectors useful for expression in the yeast *Saccharomyces cerevisiae* include pYepSecl (Baldari et al. EMBO 6:229-234, 1987) and pYES2 (Invitrogen Corp., San Diego, Calif.).

Baculovirus vectors are also available for the expression of the proteins in cultured insect cells (F9 cells). The use of recombinant Baculovirus vectors may be, or is, analogous to the methods disclosed in "Baculovirus Expression Protocol", ed. by C. D. Richardson, 1995, Humana Press Inc.; Smith et al., "Production of Human Beta Interferon in Insect Cells Infected with a Baculovirus Expression Vector," Mol Cellular Biol 3:2156-2165, 1983; Pennock et al., Strong and Regulated Expression of *Escherichia coli* B-Galactosidase in Insect cells with a Baculovirus Vector, Mol Cellular Biol 4:399-406, 1984.

Other vectors useful for expressing the SAP proteins, or an epitope of the proteins, include viral vectors. Methods for making a viral recombinant vector useful for expressing the disclosed proteins are analogous to the methods disclosed in U.S. Pat. Nos. 4,603,112; 4,769,330; 5,174,993; 5,505,941; 5,338,683; 5,494,807; 4,722,848; E. Paoletti, "Applications of Poxvirus Vectors to Vaccination: An Update," PNAS USA 93:11349-11353, 1996; Moss, "Genetically Engineered Poxviruses for Recombinant Gene Expression, Vaccination and Safety," PNAS USA 93:11341-11348, 1996; Roizman, "The Function of Herpes Simplex Virus Genes: A Primer for Genetic Engineering of Novel Vectors," PNAS USA 93:11307-11302, 1996; Frolov at al., "Alphavirus-Based Expression Vectors: Strategies and Applications," PNAS USA 93:11371-11377, 1996; Grunhaus et al., "Adenoviruses As Cloning Vectors," Seminars in Virology 3: 237-252, 1993 and U.S. Pat. Nos. 5,591,639; 5,589,466; and 5,580,859, relating to DNA expression vectors.

In accordance with one embodiment of the present invention, isolated and/or purified antibodies that recognized and bind SAP proteins may be generated for inclusion in a diagnostic device as herein described. For instance, according to one embodiment, substantially pure recombinant polypeptide suitable for use as an immunogen may be isolated from cells in which it is produced and then polyclonal antiserum containing antibodies to heterogeneous epitopes of an SAP protein may be prepared by immunizing suitable hosts with the expressed polypeptide, which may be unmodified or modified to enhance immunogenicity. As is generally known in the art, effective polyclonal antibody production may be affected by many factors related both to the antigen and the host species. For example, small molecules tend to be less immunogenic than others and may require the use of carriers and adjuvant. Also, hosts may vary in response to site of inoculations and dose, with both inadequate and excessive doses of antigen resulting in low titer antisera.

Booster injections may be given at regular intervals, and antiserum harvested when antibody titer thereof, as determined semi-quantitatively, for example, by double immunodiffusion in agar against known concentrations of the antigen, begins to fall. See, for example, Ouchterlony et al. (Handbook of Experimental Immunology, Wier, D. (ed.) chapter 19. Blackwell (1973)). In general, plateau concentration of antibody may usually be in the range of 0.1 to 0.2 mg/ml of serum. Affinity of the antisera for the antigen is determined by preparing competitive binding curves, as described, for example, by Fisher (Manual of Clinical Immunology, Ch. 42. (1980)).

Another possible approach to raising antibodies against the SAP proteins may utilize synthetic peptides synthesized on a commercially available peptide synthesizer based upon the amino acid sequence correlating to the known SAP gene sequences.

Antibodies may optionally be raised against the SAP proteins by subcutaneous injection of a DNA vector that expresses the polypeptide into laboratory animals, such as mice. Delivery of the recombinant vector into the animals may be achieved according to methods as are generally known in the art.

In another embodiment, monoclonal antibodies may be raised by hybridoma cells, phage display libraries, or other methodology. Monoclonal antibodies may be e.g., human, rat, or mouse derived. For the production of human monoclonal antibodies, hybridoma cells may be prepared by fusing spleen cells from an immunized host, e.g., a mouse, with a tumour cell. Appropriately secreting hybridoma cells may thereafter be selected according to, for example, the method of Kohler and Milstein (Nature 256:495(1975)), or derivative methods thereof. (Procedures for monoclonal antibody production are also described in Harlow and Lane (1988). Antibodies, A Laboratory Manual, Cold Spring Harbor Laboratory, New York; Cole, et al., "Monoclonal antibodies and Cancer Therapy, Alan R. Liss, Inc., pp. 77-96.). Rodent antibodies may be humanised using recombinant DNA technology according to techniques known in the art. Alternatively, chimeric antibodies, single chain antibodies, Fab fragments, and so forth may also be developed against the SAP polypeptides using skills known in the art.

The present invention may be better understood with reference to the following examples.

EXPERIMENTAL PROCEDURES

ELISA Assay

Samples containing primary antibody were screened by ELISA assay as follows: Purified protein was coated at 2 micrograms per milliliter (µg/ml) with 50 microliters (µL) per well on a 96 well flat bottomed plate for 1 hour at room temperature. Wells were then blocked in 200 µL of 1×PBS/1% BSA solution for 1-2 hours and briefly rinsed in 200 µL 1×PBS/0.02% NaN$_3$. Samples and a negative control were serial diluted at 1/50 in 1×PBS/1% BSA in duplicate and incubated for 1 hour. An HRP secondary antibody was diluted at 1/2000 in 1×PBS/1% BSA and incubated for 1 hour. Both primary and secondary antibody incubations were followed by 3 washes in 200 ul of 1×PBS/0.05% Tween 20. Color signals were developed with 50 µL of TMB solution followed within 2 to 5 minutes by 50 µL of TMB stop solution. Plates were read on a spectrophometer at 450 nm.

IgG Purification

Primary antibodies were enriched from 6 ml of crude sample using a 1 milliliter (ml) protein A agarose column. The column was attached to a peristaltic pump and the flow through was diverted through an optical reader. Crude sample was diluted in binding buffer to a total volume of 16 ml and loaded onto the column in 5 ml increments. After loading, the column was washed in 15 ml binding buffer, followed by 5 ml of elution buffer. The final eluate had a volume of 2 ml at its greatest peak. This process was repeated two times for final combined eluate volume of 6 ml. The eluate was then exchanged into 1×PBS buffer by spinning through an Amicon Ultra 15 30 kDa cutoff centrifuge filter at 4500×g.

Western Blotting

Protein samples were diluted in 1× sample buffer with 0.1M DTT and run on a 4-12% SDS-Page gel for 45 minutes at a constant 200V. Protein was then transferred from the acrylamide gel to PVDF membrane for 1 hour at a constant 30V. The membrane was blocked in 10 ml block solution of 2% BSA in 1×PBS/0.2% Tween for 1 hour at room temperature or overnight at 4° C. Purified polyclonal antibody was used at a dilution of 1/5000 in 10 ml of primary antibody dilution buffer and incubated with shaking for 1 hour at room temperature. The membrane was then washed three times in 1×PBS/0.2% Tween for 5 minutes each and then transferred to 10 ml of secondary antibody solution for 30 minutes while shaking at room temperature provided by the WesternBreeze Chromogenic Kit from Invitrogen. The membrane was washed again three times in 1×PBS/0.2% Tween for 5 minutes each. The signal was developed via incubation with 5 ml of chromogenic substrate specific for sample antibodies for 5 to 30 minutes (depending upon the desired strength of signal), followed by a final rinse in ddH$_2$O, and air drying overnight.

In Vitro SAP Expression

*Candida albicans* cells (ATCC strains 96113, 10231D, 10261, and 11006) were streaked from a glycerol stock on to a YPD agarose plate (1% yeast extract, 2% peptone, 2% dextrose) and stored at 4° C. One colony was transferred to 2 ml culture of YPD broth and grown overnight at 30° C. The culture was diluted to an O.D. value of 0.2 in 20 ml of YBD media (0.2% yeast extract, 0.2% BSA, 2% glucose) and grown at 37° C. for up to 5 days. pH was adjusted to 4.5. One milliliter samples of cells in suspension were collected at periodic time points and spun to pellet in a tabletop microcentrifuge. The supernatant was collected for western blot analysis.

SAP Purification from In Vitro *Candida* Culture

Ten milliliters of media culture supernatant collected after 72 hours of incubation at 37° C. with YBD media were flowed over a 1 ml pepstatin A agarose column pre-equilibrated with 10 ml of 0.1M acetic acid (pH 3.6), 1M NaCl. The column was attached to a peristaltic pump and the flow through was diverted through an optical reader. The column was then washed in an additional 20 ml of 0.1M acetic acid (pH 3.6), 1M NaCl and eluted with 4 ml of 0.1M Tris-HCl (pH 8.5), 1M NaCl. Samples were collected for western blot analysis from the supernatant flow through, low pH wash, and high pH elution.

Example 1

Genomic DNA from *Candida albicans* culture (ATCC strain 10231 D) was isolated and the target SAP3 gene was amplified via PCR. SAP3Δ18 was successfully subcloned into an *E. coli* expression vector, pET28 (available from Novagen) and a total of 75 mg of protein (32 kDa) was obtained from 400 ml of bacterial culture and purified using an FPLC via a c-terminal 6× histidine tag. This protein was solubilized in 6M urea and refolded via dialysis in 1×PBS.

Figure 2:
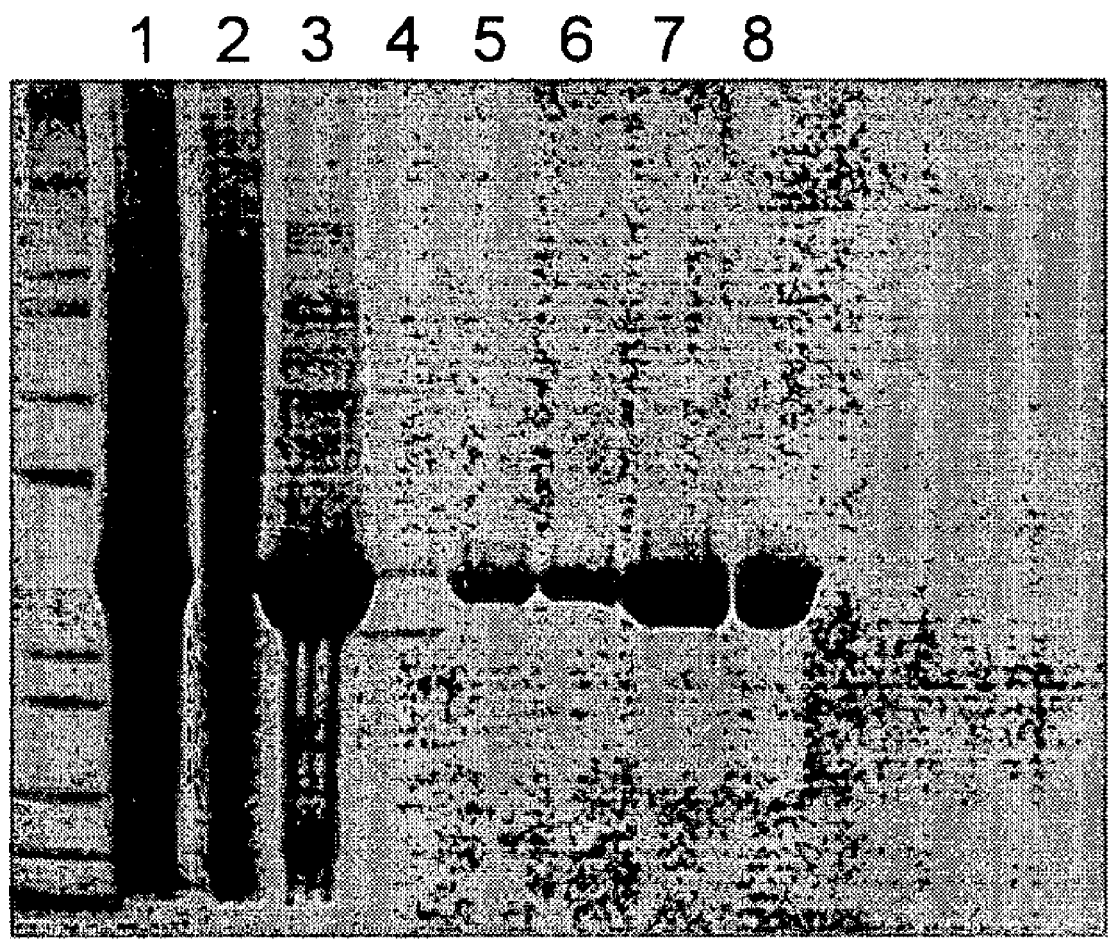
FIG. 2 illustrates the purification analysis by gel electrophoresis of recombinant SAP3Δ18 protein obtained via an *E. coli* expression system.

FIG. 2 illustrates the purification analysis of the SAP3 protein obtained. With reference to the Figure, individual lanes illustrate the following: lane 1—total lysate, lane 2—soluble fraction, lane 3—insoluble fraction, lane 4-flow through, lane 5—low imidazole wash, lane 6—high imidazole elution, lane 7—high imidazole elution, and lane 8—after dialysis.

Figure 3:
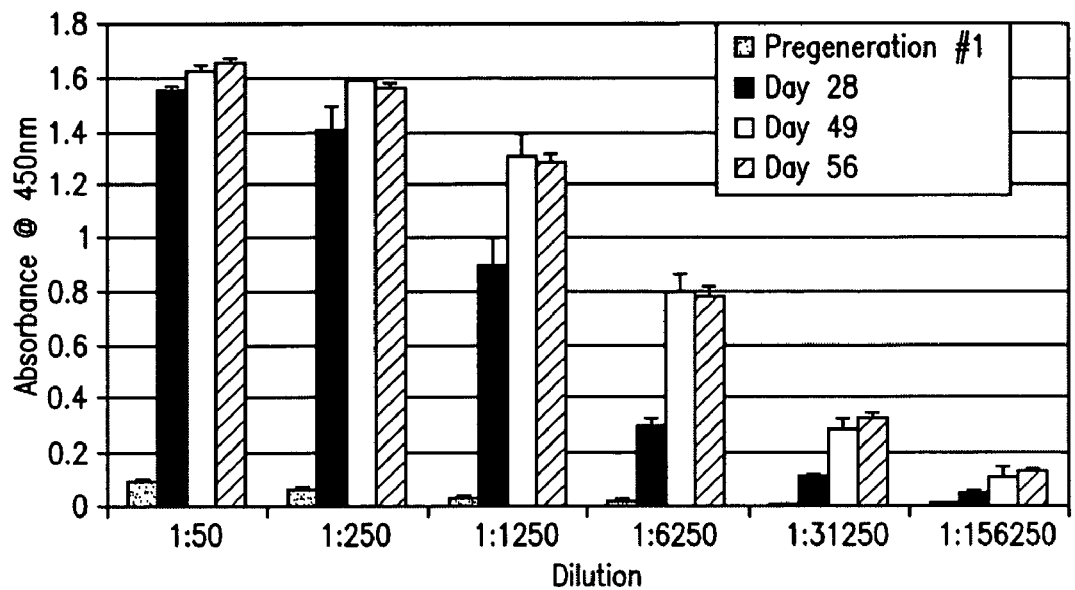
FIG. 3 graphically illustrates the Enzyme Linked Immunosorbant Assay (ELISA) results of samples obtained prior to and over the course of generation of antibodies specific to SAP3Δ18 protein, as described in the example section.
Figure 4:
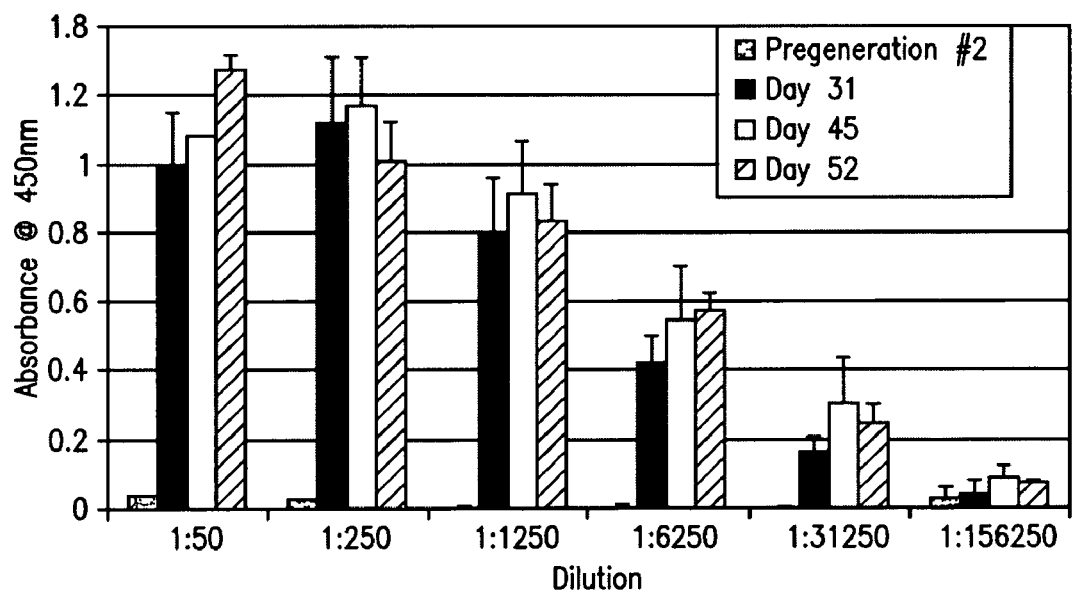
FIG. 4 graphically illustrates ELISA results of a second set of samples obtained prior to and over the course of generation of antibodies specific to SAP3Δ18 protein in a second run, as described in the example section.

IgGs were generated in two separate runs (referenced as runs #1 and #2 in the Figures and Tables). FIGS. 3 and 4 illustrate the response of the IgGs generated over the course of each run. Specifically, the figures illustrate the ELISA assay results during each run prior to IgG generation (labeled pre-generation) and at various days over the course of the run, as indicated on the graphs. As can be seen, antibody responses increased significantly over the course of the runs.

Table 2, below, presents O.D. values of ELISA results obtained during the runs. The background is recorded in the even numbered columns.

of 42 kDa is visible at 48 and 72 hours (FIGS. 8A and 8B, M indicates markers). The increase in this signal is inversely proportional to the presence of BSA protein in the media, such that as SAP proteinase expression increases, intact BSA protein decreases.

TABLE 2

|  | Sample dilution | | | | | | | | | | | |
| --- | --- | --- | --- | --- | --- | --- | --- | --- | --- | --- | --- | --- |
|  | 1:50 | | 1:250 | | 1:1250 | | 1:6250. | | 1:31250 | | 1:156000 | |
|  | 1 | 2 | 3 | 4 | 5 | 6 | 7 | 8 | 9 | 10 | 11 | 12 |
| Pre-generation run#1 | 0.12 | 0.11 | 0.073 | 0.05 | 0.04 | 0.03 | 0 | 0.019 | 0.03 | 0.05 | 0.03 | 0.02 |
| Pre-generation run#2 | 0.17 | 0.28 | 0.096 | 0.09 | 0.06 | 0.04 | 0 | 0.028 | 0.03 | 0.02 | 0.03 | 0.02 |
| run#1 Day 28 | 0.95 | 0.18 | 0.948 | 0.16 | 0.6 | 0.09 | 0.2 | 0.04 | 0.09 | 0.03 | 0.04 | 0.02 |
| run#1 Day 49 | 1.07 | 0.17 | 1.143 | 0.16 | 0.96 | 0.09 | 0.5 | 0.045 | 0.19 | 0.03 | 0.08 | 0.02 |
| run#1 Day 56 | 1.06 | 0.14 | 1.146 | 0.1 | 0.87 | 0.05 | 0.4 | 0.034 | 0.16 | 0.03 | 0.06 | 0.03 |
| run#2 Day 56 | 0.88 | 0.08 | 1.075 | 0.06 | 0.89 | 0.04 | 0.6 | 0.025 | 0.2 | 0.03 | 0.08 | 0.03 |

Figure 5:
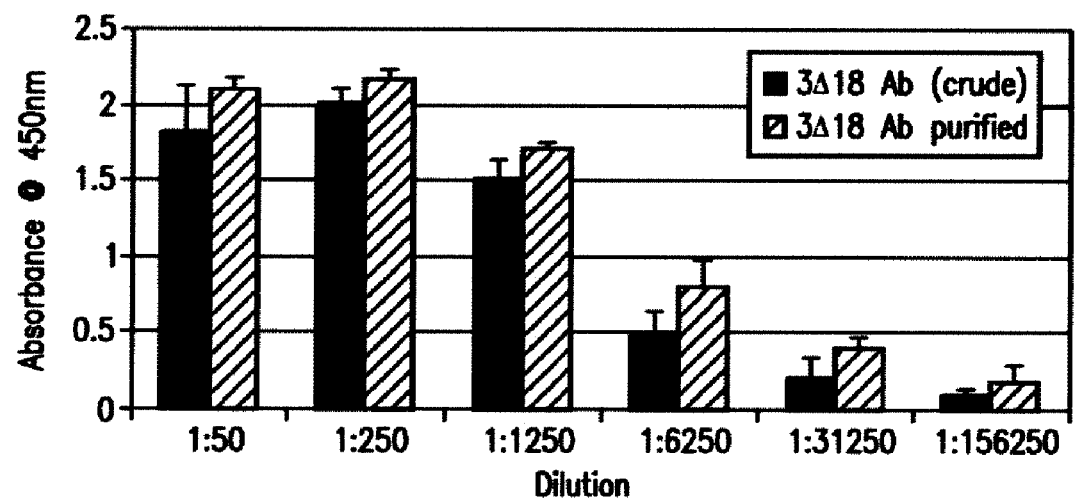
FIG. 5 compares the strength of reaction of a sample containing SAP polyclonal antibodies specific to recombinant SAP3Δ18 protein to the strength of reaction of a purified solution of the same polyclonal antibodies.

IgG was collected at day 70 in run#1 and purified using a protein A agarose column. The final volume of purified antibody was 1 ml at a concentration of 30 mg/ml. An ELISA assay comparing the strength of the reaction of the crude sample and the purified antibody to recombinant protein indicates that the purified antibody is relatively stronger at the same dilution (FIG. 5).

Figure 6:
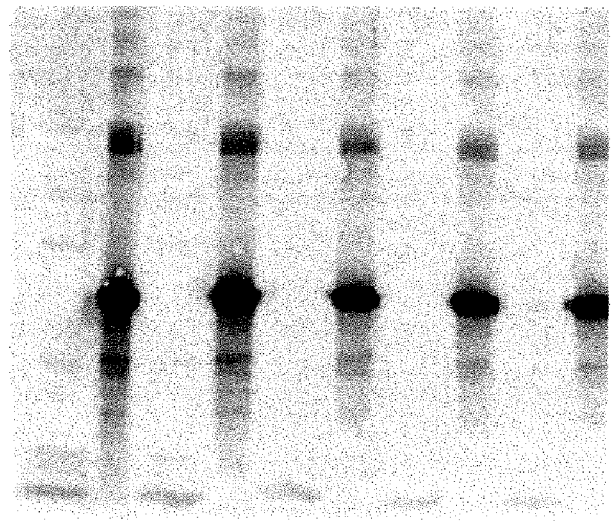
FIG. 6 illustrates the results of a western blot procedure in which the purified antibodies of FIG. 6 were probed against the recombinant SAP3Δ18 protein.

The purified antibodies were also probed against recombinant protein in a western blot. A three inch×four inch PVDF membrane was cut into five vertical strips with 1 µg of purified SAPΔ18 protein per strip. Lanes were 10 µl of markers (left lanes on FIG. 6) alternating with 1 µl of protein (right, darker lanes on FIG. 6). Each strip was probed separately at dilutions of 1/1000, 1/2000, 1/5000, 1/7000 and 1/10000. As may be seen with reference to FIG. 6, the purified SAP3Δ18 antibody gave a strong and clear signal at each dilution and, in fact, could have likely been diluted at 1/20000 or higher with continued visible signal. The bands at higher molecular weights correspond to dimers and other higher order multimers. The bands at lower molecular weights represent degradation products resulting from long-term storage of the protein at 4° C.

Example 2

Endogenous SAP proteins produced by hyphal *Candida albicans* cells in culture were detected via the polyclonal antibody developed in Example 1.

Previous studies have detected the presence of mRNA transcripts of SAP genes when bovine serum albumin (BSA) is an available food source. Ross et al. (1990) showed a peak expression of SAP proteins at 12 and 20 hours after changing cells from a standard growth media containing peptone (YPD) to a media containing 0.2% BSA (YBD). Accordingly, an in vitro culture of *C. albicans* (ATCC strain 10231 D) was induced to make the transition to hyphal cells via growth at 37° C. in YBD media. The presence of hyphal cells at 18 hours was verified by visual inspection under a microscope (FIGS. 7A and 7B).

A culture of the *C. albicans* cells was grown in 20 ml of YBD media at 37° C. with an adjusted pH of 4.5 and samples of the culture supernatant were collected at 0, 24, 48 and 72 hours. Supernatant samples were run on a 4-12% SDS-Page gel and stained with collodial blue or transferred to PVDF membrane for western blotting. A clear signal representing endogenous SAP proteins at the expected molecular weight Comparison of the collodial blue stain (FIG. 8B) with the western blot FIG. 8A) indicates that the purified antibody does not have strong reactivity to the presence of BSA in the YBD media. In the western blot, there is only a faint shadow of a signal corresponding to the relatively significant amounts of BSA protein present in the time point samples from 0 and 24 hours. At the same time, the purified SAP3Δ18 antibody is able to detect the comparatively smaller quantity of SAP protein at 48 and 72 hours, a quantity that is not actually visibly distinct in a standard collodial blue stain. This indicates that the purified SAP antibody is highly specific to SAP proteins and has little to no cross-reactivity with other media components.

The process was repeated for the other *C. albicans* strains (ATCC strains 96113, 10261, 11006) with equivalent results.

Example 3

Figures 9A, 9B:
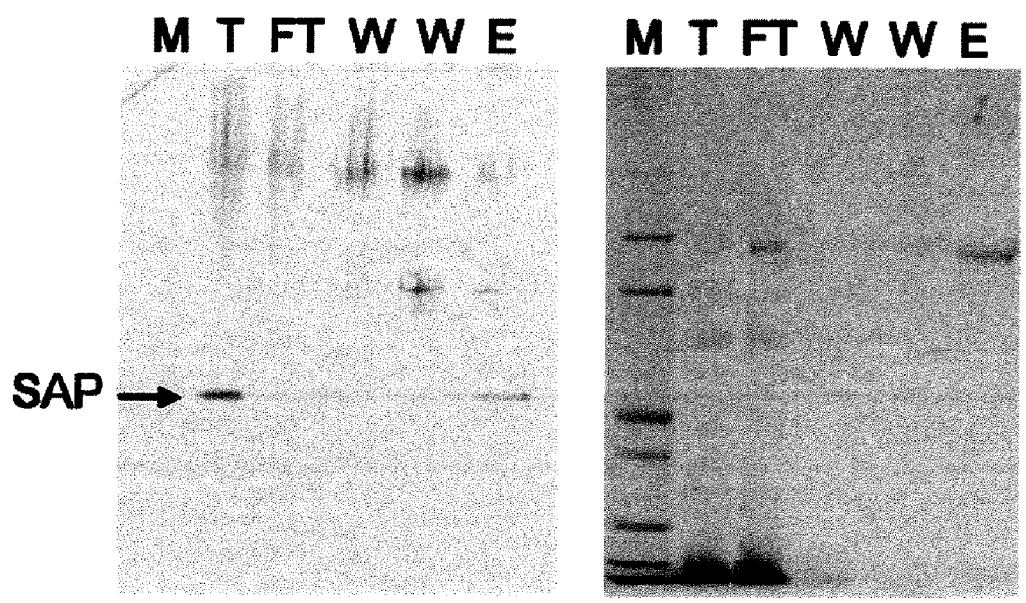
FIG. 9A illustrates the results of western blot procedures taken over time during a purification of endogenous SAP proteins from *Candida* culture supernatant, the samples were probed against purified SAP3Δ18 polyclonal antibodies generated in the example section.
FIG. 9B illustrates a collodial blue stain of the samples of FIG. 9A.

Endogenous SAP proteins were purified from culture supernatant by binding to pepstatin A immobilized on an agarose column. Pepstatin A is a tight-binding reversible inhibitor of aspartyl proteinases such as the *Candida* SAPs. Most peptidases of other catalytic types do not bind to pepstatin. 10 ml of culture of supernatant from *Candida* cells in YBD media for 72 hours at 37° C. were flowed over a pepstatin A agarose column. Protein that cannot bind to pepstatin A was washed away before a final elution of bound proteins with a high pH solution. A western blot of samples taken throughout the purification process (FIG. 9A) indicates that endogenous SAP proteins present in the original supernatant sample (total—T) successfully bound to the pepstatin inhibitor and were only released in the elution at high pH. FIG. 9B illustrates the collodial blue stain of the same samples. With reference to the figures, M=markers, T=total, FT=flow through, W=wash, and E=eluate.

The time course data combined with the purification of an aspartyl proteinase from in vitro *Candida albicans* cultures indicate that the polyclonal antibody is specifically detecting endogenous SAP proteinases. These proteins are secreted, as indicated by their presence in culture supernatants (rather than cell membrane bound), and active at an acidic pH of 4.5, the normal pH of the vagina.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A diagnostic test kit for detecting a secreted aspartyl protease protein within a test sample, the diagnostic test kit comprising:
   a lateral flow heterogeneous assay device comprising a fluidic medium, the fluidic medium defining a detection zone within which is immobilized a receptive material, wherein a test sample applied to the lateral flow assay device flows to the detection zone, and the detection zone generates a detection signal that corresponds to the presence or absence of a secreted aspartyl protease protein; and
   a detection probe conjugated with a binding member;
   wherein the receptive material, the binding member, or both contain a first antibody that is capable of specifically binding to the secreted aspartyl protease protein.

2. The diagnostic test kit of claim 1, wherein the receptive material contains the first antibody.

3. The diagnostic test kit of claim 2, wherein the binding member contains a second antibody that specifically binds to the secreted aspartyl protease protein.

4. The diagnostic test kit of claim 3, wherein the first antibody is a monoclonal antibody that specifically binds to a first epitope of the secreted aspartyl protease protein and the second antibody is a monoclonal antibody that specifically binds to a second epitope of the secreted aspartyl protease protein.

5. The diagnostic test kit of claim 1, wherein the binding member contains the first antibody.

6. The diagnostic test kit of claim 1, wherein the first antibody is a monoclonal antibody.

7. The diagnostic test kit of claim 1, wherein the first antibody is a polyclonal antibody.

8. The diagnostic test kit of claim 1, wherein the fluidic medium is a porous membrane.

9. The diagnostic test kit of claim 1, wherein the first antibody has been developed against a recombinant secreted aspartyl protease protein or an immunogenic fragment thereof.

10. The diagnostic test kit of claim 9, wherein the first antibody has been developed by a hybridoma cell that has been generated through fusion of a human tumor cell with a cell from an animal immunized with the recombinant secreted aspartyl protease protein or an immunogenic fragment thereof.

11. The diagnostic test kit of claim 1, wherein the diagnostic test kit is capable of detecting infection by *Candida albicans*.

12. The diagnostic test kit of claim 1, the lateral flow assay device further comprising an absorbent pad located downstream from the detection zone.

13. The diagnostic test kit of claim 1, the lateral flow assay device further comprising a conjugate pad located upstream of the detection zone.

14. The diagnostic test kit of claim 13, the conjugate pad carrying the detection probe in a dehydrated form, the detection probe being free to migrate upon rehydration with a test sample.

15. The diagnostic test kit of claim 1, the lateral flow assay device further defining an indicator zone.

16. The diagnostic test kit of claim 1, the lateral flow assay device further defining a calibration zone.

17. The diagnostic test kit of claim 1, wherein the conjugated detection probes or complexes thereof are separated from the test sample as the test sample flows across or through the lateral flow assay device.

* * * * *